United States Patent [19]

McRae et al.

[11] 3,978,855

[45] Sept. 7, 1976

[54] POLYURETHANE FOAM SURGICAL DRESSING

[75] Inventors: Wayne A. McRae, Salem, N.H.; Philip B. Reed, Needham, Mass.

[73] Assignee: Ionics Lyo Products Company, Watertown, Mass.

[22] Filed: Jan. 17, 1975

[21] Appl. No.: 541,809

[52] U.S. Cl. .............................. 128/156; 128/132 D; 128/268; 260/2.5 AZ; 260/2.5 AD; 260/2.5 BD; 264/321; 428/311; 428/315; 428/305; 428/338; 428/425

[51] Int. Cl.² ....................... A61L 15/00; B32B 3/26

[58] Field of Search ........... 428/311, 310, 315, 305, 428/212, 218, 338, 425; 260/2.5 AZ, 2.5 AD, 2.5 BD; 128/132 D, 156, 268; 264/321, 344

[56] References Cited

UNITED STATES PATENTS

| | | | |
|---|---|---|---|
| 3,499,811 | 3/1970 | Clarke | 428/311 |
| 3,524,755 | 8/1970 | Hochberg | 427/428 |
| 3,816,233 | 6/1974 | Powers | 428/311 |
| 3,849,238 | 11/1974 | Gould et al. | 428/315 |

*Primary Examiner*—William J. Van Balen
*Attorney, Agent, or Firm*—Norman E. Saliba

[57] ABSTRACT

The invention is directed to an open celled polyurethane foam article, which initially is generally non-absorbent, the surface of which is subsequently rendered absorbent by decreasing the average pore cell size to a critical range while preferably also simultaneously or subsequently achieving a critical range of a wetting agent in such surface. This can be accomplished in either of two ways. The first method is to permanently collapse the cells in the surface region of the original foam so that the concentration of any residual wetting agents initially present in the structure increases in the compressed surface region, thus rendering said surface more readily absorbent. For a surgical dressing, the surface cells should be permanently but only partially collapsed to substantially less than the original size to form a microporous skin. According to the second method substantially all residual wetting agents which may be present in the original foam material are extracted from the polyurethane either before or after forming the microporous skin surface. Preferably, the extraction comes after formation of the skin so that a controlled amount of a desired wetting agent(s) can then be reapplied to the microporous surface for better controlling absorbency into the structure. As the invention relates primarily to surgical dressings, a critical range for the amount of wetting agent(s) and the average cell pore size in the collapsed surface have been found which are related to the wicking, absorbency rate, and non-adherence characteristics of the resulting structure. These characteristics in turn are directly related to critical and measurable differences in the rate of epithelization, wound healing performance and wound healing quality.

18 Claims, No Drawings

POLYURETHANE FOAM SURGICAL DRESSING

A dressing material for a wound must ideally possess several properties. Such a dressing should be absorbent to remove excess exudate from the wound and at the same time be capable of protecting the wound from mechanical injury as well as reducing the risk of infection thereof by bacteria. Preferably, it should be non-adherent to the wound so as not to disturb healing during periods of inspection of the wound or removal of the dressing. Furthermore, a dressing material must be free of toxic substances which may be absorbed into the wound. While all dressings must perform certain basic functions, it has been well documented that the pattern of healing (speed and quality) can be profoundly affected by the kind of dressing used.

Commonly known cellulosic dressings, such as cotton lint, cotton gauze, cotton wool pads and cotton/rayon wool pads faced with non-woven materials demonstrate good absorbent qualities, but their surface fibers tend to adhere to the wound or to absorb the scab-forming serum so that they actually become embedded in the scab as it coagulates and hardens. Thus, if these dressings are removed to allow inspection or treatment of the wound, the wound tissue or scab may be damaged, retarding the healing process and even re-opening the wound. Furthermore, the open weave construction of these dressings and the uncontrolled absorbency rate of the cellulosic fibers causes the serous exudate on the wound surface to dry out. The epidermis regenerating from the wound edges and from cut surfaces of hair follicles within the wound is then forced to move through the fibrous tissue beneath the dry layer which formed the scab and the epitherlization rate is thus substantially slower than if the epithelium were allowed to move through a moist fluid layer.

Attempts have been made to provide wound dressings of fully occlusive materials, such as polyethylene, in order to keep the wound area from dehydrating. Such dressings provide a satisfactory environment for skin regeneration by preserving a fluid layer of serum in the vicinity of the wound. Epithelization rate under these occlusive conditions has been shown to be at least twice as rapid as with the fibrous cellulosic dressings. However, it is essential to apply such fully occlusive dressings in a sterile state and under sterile conditions to prevent harmful bacteria from entering the wound area and breeding close to or in the wound. Furthermore, such dressings do not absorb exudate, thus causing pooling in the wound which is not desirable.

The use of polyurethane foam as a partially occlusive dressing has been attempted in the past as well. Such dressings however made from Bowater-Scott's "Sterafoam" and Harrison and Jones' "Supersoft" have an open-cell structure with relatively enormous pores (greater than 200 micrometers) compared to the tissue fibers and cells on the wound surface. The serous exudate will penetrate these dressings only under pressure, filling the large open cells with proteinaceous fluid, erythrocytes, and leucocytes. Histological evidence shows that the exudate on the wound surface will generally remain moist for at least a few days with the regenerating epidermis migrating through the moist exudate between the wound surface and the overlying dressing. By preserving this moist environment while epidermal migration is taking place, epithelization is relatively rapid compared to wounds covered with conventional cellulosic dressings. However due to the excessive cell pore size of such foam, relative to the tissue cell size, it is necessary to press such nonmodified open-celled polyurethane foam dressing against the wound to physically drive serum into the dressing to overcome the surface tension of the serum and allow excess exudate to be removed. The polyurethane foam cell structure becomes impressed into the dermis, indenting the collagenous tissue, and causing numerous inflammatory cells to be attracted to this foreign material. The relative difference between foam cell size and tissue cell size also allows the regenerating epidermis to grow around the particles of polyurethane foam. This stimulates hyperplasia resulting in bizarre epidermal tissue. In some cases, particles of foam are broken away from the large open-celled dressing and come to lie in the developing connective tissue under the new epidermis causing foreign body reactions. In addition such indentation of the wound surface with inclusion of particles of polyurethane within the epidermis and dermis may also lead to excess fibrosis, granuloma and scarring.

In some cases, non-adherent wound dressings have been made by placing a normally occlusive material, such as polyethylene, over the front surface of an absorbent pad, such as cotton gauze. To perform properly, the occlusive surface contains perforations or is spatially apertured to allow exudate to migrate into the absorbent backing. While such a structure partially overcomes the problems of adherence to the wound as commonly found in cotton gauze dressings and of foam particles embedding in the wound, the uncontrolled absorption of the pad causes the wound area to dry out, scab formation to occur, and the epithelization rate to be retarded by forcing the regenerating epithelium to migrate beneath the dry necrotic region.

It is therefore an object of the present invention to provide improved polyurethane surgical dressings which allow for a more satisfactory microclimate for tissue regeneration and a resultant epithelization rate at least twice as rapid as conventional cellulosic dressings.

Another object is to provide a dressing with at least one absorbent microporous surface, in which the cell pore size range is controlled, to render the surface non-adherent to the wound area and eliminate foreign particles becoming embedded in the wound.

Another object is to provide a dressing in which the concentration of wetting agent(s) is maintained within a critical range to more readily control the absorption of excess exudate to prevent pooling of serum in the vicinity of the wound, but to still maintain a moist fluid layer between the wound surface and the dressing within which regenerating tissue can migrate.

A further object is to provide a process to permanently but only partially collapsing a surface of a normally non-absorbent polyurethane foam to form an integral microporous surface thereon which surface is thereby rendered absorbent due to the decreasing of the surface area per unit foam weight and also preferably increasing the concentration of wetting agent per unit foam surface and further controlling these ranges within certain critical parameters to provide a unique microclimate for improved wound healing.

Various other objects and advantages will be apparent to one skilled in the art upon reading the following disclosure and the novel features will be particularly pointed out hereinafter in connection with the appended claims. It is understood that the details may be modified without departure from the principles of the invention which is readily understood when taken in connection with the accompanying description and examples.

Various processes for subjecting polyurethane foams to heat and pressure are well known in the prior art and it is to be understood that the present invention does not claim as novel such processes in general or articles produced thereby. Rather the preferred embodiment provides a polyurethane foam article, the foam cells on at least one surface being pemanently but only partially collapsed compared to the remaining portions of the foam article and which surface is further rendered more readily absorbent by concentrating or adding an amount of wetting agent per unit surface into the collapsed membrane surface relative to cells in the remaining portions of the foam article; the cell pore size of said surface being critically controlled preferably in conjunction with the concentration of wetting agent(s) to produce a unique wound dressing which provides a satisfactory microclimate for tissue regeneration and improved wound healing.

The article described in this present invention is fabricated from an original base material of an open-celled polyurethane foam having cells of an average pore size in the range of about 200 to about 2,000 micrometers and containing in one of the preferred embodiments of the invention a residual concentration of wetting agent(s). The article further comprises a microporous surface region of open cells which have been permanently partially collapsed from that of the original base cells so that the average pore cell size in said surface region is between about 0.2 to 200 micrometers and preferably containing a concentration of wetting agent in said microporous surface of no greater than about 1% and preferably no less than about 0.01 percent by weight.

It is found that if the average pore cell size of the original foam base material is less than about 200 micrometers the entire structure including the modified and non-modified portions will continue to wick up exudate and the modified microporous polyurethane surface next to the wound will dry out, this substantially preventing development of the proper environment for epithelization and tissue regeneration. In contrast should the cell pore size of the original foam structure employed to fabricate the unique dressing material of the present invention be greater than about 2,000 micrometers, it is found that excess exudate will not be held in the non-modified foam portion of the dressing and will instead tend to flow out into the environment making the article an unsatisfactory wound dressing. The critical range of about between 200 to 2,000 micrometers for the original non-modified foam portion was found in practice to be the ideal range for maintaining the adjacent modified microporous surface in a reasonably moist state with the non-modified back up foam further functioning as a reservoir for holding excess exudate therein. The pore size of polyurethane cellular material may be controlled or varied as desired by well known and conventional means such as for example in the case of isocyanate derived polymers by the addition of foam stabilizing or coalescing agents.

It is further found that if the wetting agents(s) on the modified microporous polyurethane foam surface constitute less than the preferred minimum of about 0.01% by weight, the article will not readily absorb exudate into its structure thereby tending to cause pooling of serum below the microporous foam surface cover which further causes maceration of tissue in the wound area. Should the wetting agent(s) contained in the microporous foam surface become greater than about 1% by weight, it is found in tests conducted on pigs that wounds dry excessively and the rate of epithelization is increasingly slower as the level of wetting agents(s) increases above the 1% level.

The foam cells comprising the microporous surface have been defined as "permanently but only partially collapsed." It is known that polyurethane foam can be reversibly deformed or compressed to reduce thickness up to a certain extent but will essentially recover its original thickness upon washing or steam heating. The present invention relates to compression of the surface of the foam at an extended temperature beyond this pre-determined extent, that is, to an "irreversible" (permanent) process. The open cells defined as "partially collapsed" have their standard structural members (polymer strands) distorted to produce smaller cells or pores, but it is important that the cells are not completely collapsed or fused. So as not to have an average pore cell size less than about 0.2 micrometers, the temperature of the polyurethane foam employed in the present process may exceed its second order transition point or glass temperature but not exceed the first order transition temperature for the specific polymer and pressure applied. Such an effect is produced by controlling the temperature and pressure parameters employed.

The foam article of the present invention is preferably in the form of a sheet, strip or ribbon and one or both of the major surfaces of the foam thereof may be increased in density. Where both surfaces of the foam are of increased density, the densities of the two surfaces may be the same or different.

According to a further aspect of the invention there is provided a process for making an open-celled polyurethane foam article which comprises applying pressure and heat to at least a surface of the foam to permanently (irreversibly) partially collapse the foam cells on said surface to an extent such that said surface is or may be rendered absorbent. The cells on said surface must be permanently but only partially collapsed to produce a microporous surface having an average pore size no greater than about 200 micrometers and preferably containing therein at least about 0.01% by weight of wetting agent to overcome the surface tension of blood, serum, water, and other fluid exudate. The surface pores must also be larger than about 0.2 micrometers to allow proper wicking and absorption of said exudate to pass through the collapsed surface membrane. The foam cells remote from said surface remain unchanged at a pore size greater than about 200 micrometers so as not to be readily absorbent but to still allow excess exudate to be rejected from said collapsed microporous surface into the remote, unchanged cells of the original foam and held therein as if in a reservoir.

The surface of the foam which is to be partially collapsed must be heated to a temperature near the softening point of the foam. This varies with foam composition and the surface temperature may suitably be from 300°F to 450°F depending on the time the foam is subjected to heat and pressure. It is important not to exceed the fusion temperature of the particular foam since this would cause complete collapse of the cells. The pressure applied may, for example, be up to 200 pounds per square inch and is preferably from 50 to 100 p.s.i.

This heat and pressure may be applied to said surface by conventional means such as a heated plate or roller. During the pressure and heat treatments, a release material, for example, silicone coated paper or a sheet of Teflon fluorocarbon, may be placed between the heating means and the said surface of the foam to prevent adhesion of the foam material to the plate or roller and maintain the smooth microporous membrane surface thus created.

The initial or starting piece of foam may be of any thickness but is preferably from about 0.1 cm to about 10 cm and is preferably modified by heat and pressure to a final thickness of from about 0.05 cm to about 5 cm, preferably with a compressed microporous surface thickness up to about 5 mm. From a practical standpoint, to obtain a one sided microporous surface in the desired pore size range, the foam material is usually reduced to about half its original thickness. However, this is not essential; very thin pieces of foam material, approximately 0.1 cm in thickness, can be rendered absorbent by this process and it is only necessary to modify the surface to a depth of about 0.04 mm to achieve a satisfactory result.

The foam sheet, strip or ribbon may be similarly modified on both faces for which purpose the foam, after being removed from between the plate or roller and the release material, (if present) conveniently is reversed and the operation repeated. Alternatively, the pressure plate may be heated to the foam modifying temperature so that both surfaces of the foam or even the full thickness of the foam may be modified by heat and pressure in one or more pressing and heating operations.

The foam which is employed in the invention may be a reticulated or non-reticulated, open-cell polyurethane foam based on polyester or polyether which foam is essentially non-absorbent in that any residual wetting agent(s) remaining in the foam during manufacture does not exceed 1 percent by weight of the foam. By permanently but only partially collapsing the surface of such an open-celled foam to a microporous membrane structure of the critical pore sizes as previously defined, the density or surface area per gram weight of foam is decreased. This modification in density also increases the concentration of any residual wetting agent present in the original foam, thus rendering said surface more readily absorbent. By reducing the original piece of foam to approximately one half its initial overall thickness by partially collapsing the cells of one surface, the weight of residual wetting agent(s) per unit surface in the said modified surface can be increased approximately up to ten times its original weight per unit surface.

The use of the article of the present invention as a surgical dressing in animal research on pigs indicates that the level of wetting agent(s) contained in the microporous surface of the polyurethane foam should preferably not exceed about 1 percent by weight. Beyond that level, most wetting agents appear to be at least slightly toxic to epidermal cells on the wound surface and to impair epidermal regeneration. While epidermal regeneration is still significantly more rapid under the polyurethane foam article at slightly above the said 1 percent level than wounds covered under cellulosic cotton dressings, the quality of wound healing is progressively degraded as the concentration of wetting agents in the surface increase above such concentration level.

Wound healing can also be impaired if excess exudate from a wound does not flow relatively freely into the microporous foam surface but is allowed to pool in the vicinity of the wound. If pooling is prolonged, maceration of the wound may occur and healing will break down and the wound becomes unmanageable. Therefore, although certain improved healing characteristics attributable to the article of this invention may at times be obtained in the absence of any appreciable wetting agent, (provided of course that the critical porosity range is maintained) however the minimum level of wetting agent(s) desired in the said microporous surface of the polyurethane foam dressing is still preferably above the 0.01 percent by weight to permit the exudate to be immediately absorbed into the microporous membrane surface at a relatively controlled, even rate.

Applicants have attempted to determine the physical and chemical characteristics which will predict that a particular open-celled polyurethane foam which is generally essentially non-absorbent can be rendered to produce a surgical dressing that will provide a proper microclimate for tissue regeneration and enhance wound healing. In general, it is necessary to perform preliminary tests with any given sample of foam, but preferred formulations of reticulated or non-reticulated, polyester and polyether open-cell polyurethane foams are cited in the examples. The bulk density, cell size, and thickness of the initial foam material may be chosen for the particular application for which the absorbent product is required, but the average pore cell size of the initial material should be maintained in the critical range of from about 200 to about 2,000 micrometers. If polyurethane foams are selected having residual levels of wetting agents(s) which fall outside the critical or preferred range, the level can be easily adjusted. This readjustment can be made by substantially completely extracting any residual wetting agent(s) remaining in the original polyurethane foam after manufacture. The desired concentration of wetting agent can be reapplied to at least the modified surface area and dispersed therein in an even omnidirectional pattern substantially throughout the microporous region. Suitable examples of wetting agents include anionic, nonionic and cationic surfactants singly or as mixtures, such as long chain hydrocarbon sulfates or sulfonates, e.g., sodium laurel sulfate, or long chain hydrocarbon radicals attached to polyethylene oxide radicals, such as nonylphenol poly (ethyleneoxy) ethanol (e.g., Igepal CO-730). A particularly satisfactory wetting agent is the ammonium salt of a sulfate ester of a alkylphenoxypoly ethanol sold under the trademark Alipal CO-416 (Antura Chemical Co.). For use especially in a surgical dressing article, the wetting agent could be for example polyvinyl pyrollidone, (Propylan 8123) polyoxypropylene glycol, (Carbowax 200) polyethylene glycol, (Alipal CO-436) or similar F.D.A. approved wetting agents capable of enhancing the absorbtion of serum exudate from a wound. A satisfactory method of applying the wetting agent to the foam is by dipping the foam in the desired solution of a wetting agent and carefully wringing out the excess and drying in a vacuum at 110°c. The concentration of wetting agent in the dried foam can be determined by the volume of solution dried out in the foam.

As previously stated the foam articles of the present invention are particularly advantageous for use as surgical dressing materials. In this respect, the product can be readily sterilized, for example, by means of steam autoclave, gamma irradiation, or ethylene oxide. Also, the body of the dressing material is suitable for incorporating a medicament such as an anti-bacterial and/or antiseptic. The dressing may be impregnated with such a medicament after the heat and pressure treatment but prior to sterilization. The dressing may be treated by depositing a film of medicated material on to the dressing or by dipping the dressing into a solution of medication material and then drying the material.

For purposes of this disclosure the term "residual" wetting agent is a wetting agent which may be found present in the original foam material after manufacture. For example, in the manufacture of a polyether based polyurethane, an excess amount of a polyether polyol such as polyoxypropylene glycol may be employed in the formula mix. After polymerization of the mix into the foam material there will be found residual or excess polyol that did not react. Thus the amount of residual (unreacted) polyol (wetting agent) in the foam may be brought to various levels by controlling the amount included in the initial mix or formulation. However it is difficult to exactly control the quantity of unreacted wetting agent that will remain in the newly manufactured foam by the residual method. It is therefor preferred that the foam material be firt treated by a solvent extraction process to remove all wetting agents present if any and then to reapply the wetting solution therein under controlled conditions up to any amount desired.

The following examples show, by illustration and not by limitation, the methods and materials which can be utilized in fabricating open-celled polyurethane foam articles of the present invention by employing an original foam material having average cell pore sizes of more than about 200 micrometers but less than about 2,000 micrometers and which initial foam material is generally non-absorbent, the surface of which is subsequently rendered absorbent by decreasing the average cell pores sizes to the critical range between about 0.2 to about 200 micrometers and preferably simultaneously or subsequently achieving a concentration of wetting agent(s) in said modified surface of between about 0.01 to 1.0% by weight.

EXAMPLE I

A loaf of polyurethane foam based on polyether is manufactured from the following formulation by means well known in the art:

| Ingredients | Parts by Weight |
| --- | --- |
| Polyoxypropylene glycol (a polyether polyol) | 100 |
| Stannous Octoate | 0.25 |
| Water | 4.0 |
| Dimethylethanolamine | 0.5 |
| Silicone Surfactant | 2.0 |
| Trichloromonofluoromethane | 15.0 |
| Toluene diisocyanate(80% 2,4–20% 2,6 isomer) | 82.5 |

By photomicroscopy the average pore size of the foam so produced is found to be in the critical range of between about 200 to about 2,000 micrometers. A residual wetting agent of polyol remained in the foam after manufacture as determined by extraction with ethanol in a Soxhlet extractor.

A sheet of foam is cut from the loaf in a conventional manner. A silicone coated release paper is placed on one surface of the sheet which is then placed in contact with a metal platen heated to a temperature in the range between 380° to 410°F. A cold pressure plate is forced against the free face of the foam, pressing the foam against the heated platen. A pressure of about 70 p.s.i. is maintained for about 20 seconds, at which time the cold pressure plate is removed and the sheet of modified foam is stripped from the silicone paper. The temperature employed in the heated platen is adjusted to result in the formation of a permanently, but only partially collapsed skin having an average pore size in the critical range of from about 0.2 to about 200 micrometers and a skin concentration by weight of polyol wetting agent falling within the critical range of 0.01 to 1.0 percent.

EXAMPLE 2

The heat and temperature procedure of Example 1 is repeated using a polyether foam manufactured from a slightly modified formulation:

| Ingredients | Parts by Weight |
| --- | --- |
| Polyoxypropylene glycol (a polyol) | 100 |
| Stannous Octoate | 0.4 |
| Water | 2.8 |
| Dimethylethanolamine | 0.7 |
| Silicone oil | 1.6 |
| Trichloromonofluoromethane | 13.0 |
| Toluene diisocyanate (80/20 isomer) | 36.9 |

It is found that the resulting article has pore cell size and concentration of polyol wetting agent in the required and preferred critical ranges.

EXAMPLE 3

The original non-modified polyether foams of Examples 1 and 2 containing a residual polyol wetting agent of less than 1% by weight are found substantially non-absorbent in that water when applied to the foam beads up and stands on the surface thereof. As previously stated the average pore size of the original open-celled foam structure is greater than about 200 micrometers. After the heat and pressure treatment described in Example 1, approximately half of the foam sheet thickness is permanently but only partially collapsed into a microporous surface skin having cell pore sizes in the range of between about 0.2 to about 200 micrometers. After the heat and pressure treatment, the concentration of wetting agent in the modified surface is found by extraction to be above 0.01% by weight but less than 1.0% by weight. The time, temperature, and pressure applied to the foam surface during compression, is previously determined by preliminary tests so as to allow the foam to pass into its second order transition temperature but not to substantially exceed its first order transition temperature which could lead to fusing. A standard wet-out test is performed by applying water on the partially collapsed surface of the foam which is significantly smoother than the original surface of the parent foam. Absorption is readily apparent with the water diffusing rapidly into the microporous surface within a matter of several seconds after application. The standard wet-out test is repeated on the non-modified side of the original foam and such foam is shown to remain substantially non-absorbent.

The surfaces of the microporous modified foams are completely wetted by the continuous application of water onto the surface after initial wet-out. The water is absorbed uniformly along the total surface indicating no differential in the $x$ or $y$ direction (width or length direction) and no fluid paths are found further from the center of the water application in any direction along the surface indicating uniformity of pore size distribution. Upon supersaturation of the smooth modified surface, the water is subsequently rejected therefrom and passed into the adjacent macro-celled portions of the un-modified foam. As water continues to be applied onto the microporous surface, it will continue to pass into the reservoir portion of the un-modified foam indicating a one-way valving effect, possibly the result of the foam density differential in the $z$ direction (the direction of thickness of the foam). Possibly the density differential creates a capillarity effect throughout the modified structures, the force of which is sufficiently large to overcome the surface tension of the liquid or water against the non-absorbent macroporous foam cells to allow liquid to penetrate these large open cells by displacing the air previously occupying them. It is significant to note that the modified foam surface continues to absorb water and reject and pass only excess liquid into the adjacent non-absorbent macro-cells. It is subsequently shown by experiments on pigs that pooling of serum in the vicinity of a wound with resultant maceration is avoided as the modified surface of the foam dressing exhibits rapid absorptive capacity while still allowing the microporous surface in contact with the wound to remain moist, thus providing a proper microclimate for epithelization.

EXAMPLE 4

The same heat and temperature procedure of Example 1 is repeated using a polyether based polyurethane foam manufactured from the following formulation:

| Ingredients | Parts by Weight |
| --- | --- |
| Oxypropylated glycerin (a polyether) | 100 |
| Stannous Octoate | 0.25 |
| Water | 4.0 |
| Dimethylethanolamine | 0.1 |
| Silicone Surfactant | 1.5 |
| Toluene Diisocyanate (80/20 isomer) | 49.8 |

Again the procedure employed is found to produce a product in the critical cell size but containing wetting agent outside the critical range.

EXAMPLE 5

The same heat and temperature of Example 1 is repeated using a foam based on a polyester manufactured from the following formulation:

| Ingredients | Parts by Weight |
| --- | --- |
| Polyester of adipic acid, trimethyl propane & diethylene glycol | 100 |
| Toluene diisocyanate (80% 2,4 – 20% 2,6 isomer) | 53.5 |
| N-ethylmorpholine | 2.0 |
| Water | 4.3 |
| Ammonium oleate | 1.5 |
| Coupling agent (Witco FOMEZ 77-86 non-ionic/anionic surfactant blend containing polyol, alcohol, carboxylic acid esters and oil soluble sulfonates | 1.5 |

The finished polyester based foam article is found to contain cell sizes that fall in the critical range required for the proper functioning of both the modified and non-modified portion of the foam.

EXAMPLE 6

The same procedure of Example 1 is repeated using reticulated (skeletonized) polyurethane foams having as much as 97% void area and available commercially under the trademark Scottfoam from Foam Division, Scott Paper Co., Chester, Pa. The samples of reticulated foams are identified by the manufacturer as polyester and polyether polyurethane foams. The foam samples as obtained from the manufacturer are all found to have average pore sizes within the critical range of 200 to 2,000 micrometers. The heat and temperature procedure is successful in partially collapsing a surface into a microporous structure possessing cell sizes falling within the preferred ranges.

EXAMPLE 7

The modified foams of Examples 1, 4, 5 and 6 are subsequently extracted with ethanol in a Soxhlet type extractor to substantially remove all wetting agents contained therein. Such treatment does not change the pore size of the modified surfaces of the foams. Standard wet-out tests can be performed and the modified surfaces will be found to absorb but not very readily. Various amounts and kinds of wetting agents are reapplied to the surfaces in measured doses to establish the critical minimum level at which the structures readily absorb fluids within a matter of several seconds. It is found that a minimum dose level approximately equivalent to not less than 0.01% of the weight of the modified surface is required to once again render the surface membranes very readily absorbent. Various wetting agents used include Lankro Chemical, Ltd.'s Propylan 8123, Union Carbide's Carbowax 200, and Antara Chemical's Alipal CO-436. The wetting agents are preferably applied by first dissolving in a suitable solvent such as a 90/10 ethanol/water mixture and applying the desired amount to the foam before or after head treatment. A measured volume of the wetting agent solution may be worked into a weighed amount of foam to obtain the required concentration. Alternatively, the foam may be immersed in the solution and the excess pressed or wrung out. In any case, the solvent is allowed to evaporate leaving the detergent substantially evenly distributed throughout the foam or throughout the microporous surface of the foam depending upon the manner of application of the solution. The concentration of wetting agent in the foam is controlled by adjusting the concentration of such agent in solution and/or by adjusting the amount of solution applied per unit weight of foam or per unit weight of microporous surface. The wet-out tests show the samples to be very readily absorbent on their modified microporous surfaces.

EXAMPLE 8

The modified foams described in Example 7 are doped with levels of various wetting agents above the 1 percent concentration for subsequent testing on pigs to determine the effect on wound healing at the increased concentrations. It is found that in using dressings made from samples of higher concentrations, epithelization is not as rapid when compared to dressings containing less than about 1% by weight of wetting agents(s) in the microporous surface. No fundamental differences are found among samples containing different wetting agents at substantially the same doping levels.

EXAMPLE 9

The Scottfoam polyether and polyester polyurethane foams of Example 6 which are found to have the preferred averaged pore size range of about between 200 micrometers and 2,000 micrometers, are modified on their surface by heat and pressure as described in Example 1 until the cell pore size is in the preferred range of 0.2 micrometers to 200 micrometers. The level of wetting agent is found to be outside the preferred range. The material is subsequently extracted of substantially all wetting agents and a desired volume of a wetting agent solution is re-applied in the preferred range of about 0.01 to 1% by weight. After drying, the samples are subjected to wet-out tests and found to be acceptable.

The embodiments of the invention in which an exclusive property or privilege is claimed are defined as follows:

1. An integral, non-laminated, non-rigid, open cell polyurethane foam wound dressing article comprising at least one dense surface with essentially all of said surface having a microporous structure of an average pore cell size between about 0.2 to 200 micrometers in contrast to the remaining less dense macroporous portions of the foam having an average pore cell size range between about 200 - 2,000 micrometers, said microporous surface further characterized by an absorbent structure, readily absorbent to water and fluid exudates and comprised of permanently but only partially collapsed or compressed open foam cells as contrasted to the said remaining macroporous foam cell portions which are substantially uncollapsed and non-absorbent.

2. The foam article of claim 1 comprising a non-reticulated open cell structure.

3. The foam article of claim 1 comprising a reticulated open cell structure.

4. The article of claim 1 wherein the said dense surface portion contains a wetting agent in a concentration by weight of between about 0.01 to 1%.

5. The article of claim 4 wherein the wetting agent is selected from the group consisting of an anionic, nonionic and cationic surfactant or mixtures thereof.

6. The article of claim 4 wherein the less dense foam portion also contains a wetting agent and wherein the concentration of said wetting agent in said, dense surface portion is between 1 to 10 times the concentration contained in the said less dense foam.

7. The article of claim 1 for use as a medical dressing swab.

8. The article of claim 1 for use as a surgical dressing for treating wounds in mammals.

9. The article of claim 8 wherein in a medicament is incorporated therein.

10. The process for producing an absorbent structure on a surface of an essentially non-absorbent, non-rigid, open-cell macroporous polyurethane foam starting material having an average pore cell size range between about 200 - 2,000 micrometers comprising applying sufficient heat and pressure to said foam surface to result in permanently but only partially collapsing the surface cells into a dense microporous integral structure having an average pore cell size range between about 0.2 to 200 micrometers whereby essentially all of said denser surface structure is readily absorbent to water and fluid exudates as contrasted to the remaining untreated macroporous foam cell portions which are essentially non-absorbent.

11. The process of claim 10 wherein the original non-absorbent, macroporous polyurethane foam starting material contains residual wetting agents therein and which agents by the application of heat and pressure forming the collapsed microporous surface becomes concentrated therein in an amount between about 0.01 to 1% by weight of the resulting microporous polyurethane surface structure whereby said surface becomes more readily absorbent.

12. The process of claim 11 wherein the foam material is treated by solvent extraction to remove residual wetting agents which may be present and thereafter reapplying a controlled amount of the desired wetting agent therein.

13. The process of claim 12 wherein the amount of desired wetting agent is applied after the formation of said dense microporous surface in an amount between about 0.01 to 1% by weight.

14. The process of claim 12 wherein the solvent extraction is performed on the original foam material prior to the formation of the said microporous surface.

15. The process of claim 12 wherein the solvent extraction is performed on the foam material after the formation of the said microporous surface.

16. The process of claim 12 wherein the wetting agents are selected from the group consisting of an anionic, nonionic and cationic surfactant or mixtures thereof.

17. The process of claim 10 wherein the heating of the foam is between said foams second and first order transition temperatures.

18. The process of claim 12 wherein the wetting agent is selected from the group consisting of polyethylene glycol, polyoxypropylene glycol, oxypropylated glycerin, polyvinyl pyrollidone and mixtures thereof.

* * * * *